(12) United States Patent
Davis (10) Patent No.: US 9,113,849 B2
(45) Date of Patent: Aug. 25, 2015

(54) DETACHABLE RATCHETING SHAFT FOR SPECIMEN RETRIEVAL BAG

(71) Applicant: Covidien LP, Mansfield, MA (US)

(72) Inventor: Emily Davis, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/681,615

(22) Filed: Apr. 8, 2015

(65) Prior Publication Data

US 2015/0209021 A1 Jul. 30, 2015

Related U.S. Application Data

(62) Division of application No. 13/645,544, filed on Oct. 5, 2012, now Pat. No. 9,017,340.

(60) Provisional application No. 61/550,549, filed on Oct. 24, 2011.

(51) Int. Cl.
*A61B 17/22* (2006.01)
*A61B 17/00* (2006.01)

(52) U.S. Cl.
CPC . *A61B 17/00234* (2013.01); *A61B 2017/00287* (2013.01); *A61B 2017/00407* (2013.01)

(58) Field of Classification Search
CPC ........ B65D 35/10; B65D 35/32; B65D 35/02; B65D 35/28; A61B 17/00234; A61B 17/221; A61B 2017/22121
USPC .................. 606/110, 111, 112, 113, 127, 200; 222/99, 100, 107; 383/9, 21, 19, 39, 383/51, 68, 69, 88, 89, 90, 91, 82, 83, 85; 43/11; 425/466
See application file for complete search history.

(56) References Cited

U.S. PATENT DOCUMENTS

| 3,473,698 | A | * | 10/1969 | Ballin | 222/100 |
|---|---|---|---|---|---|
| 5,190,555 | A | | 3/1993 | Wetter et al. | |
| 5,354,303 | A | * | 10/1994 | Spaeth et al. | 606/128 |
| 5,681,324 | A | | 10/1997 | Kammerer et al. | |
| 6,228,095 | B1 | | 5/2001 | Dennis | |
| 9,017,340 | B2 | | 4/2015 | Davis | |
| 2011/0182533 | A1 | * | 7/2011 | Scott | 383/119 |
| 2011/0184430 | A1 | * | 7/2011 | Parihar et al. | 606/114 |
| 2011/0184436 | A1 | * | 7/2011 | Shelton et al. | 606/114 |

FOREIGN PATENT DOCUMENTS

| WO | 2007/048078 A1 | 4/2007 |
|---|---|---|
| WO | 2011/090862 A2 | 7/2011 |

OTHER PUBLICATIONS

European Search Report dated Mar. 6, 2013 from counterpart EP Application No. 12189517.1 (7 pgs.).

* cited by examiner

*Primary Examiner* — Jonathan W Miles
*Assistant Examiner* — George J Ulsh (57) ABSTRACT

A system for retrieving a specimen includes a collapsible bag having a first mating member and a retrieval device having a second mating member. The second mating member cooperates with the first mating member for coupling the collapsible bag with the retrieval device. A rotation mechanism is disposed in the retrieval device. Actuation of the rotation device collapses an excess portion of the collapsible bag.

8 Claims, 7 Drawing Sheets

DETACHABLE RATCHETING SHAFT FOR SPECIMEN RETRIEVAL BAG

CROSS REFERENCE TO RELATED APPLICATION

The present application is a divisional application of U.S. patent application Ser. No. 13/645,544, filed on Oct. 5, 2012, which claims the benefit of and priority to U.S. Provisional Application Ser. No. 61/550,549, filed on Oct. 24, 2011, the entire contents of each of which are incorporated herein by reference.

BACKGROUND

1. Technical Field

The present disclosure relates to a surgical system for use in minimally invasive procedures. More particularly, the present disclosure relates to a system for a retrieval of a specimen from a minimally invasive surgical site.

2. Background of the Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g., nephrectomy, cholecystectomy and other such procedures. During such procedures, it is common that affected tissue or organ must be removed via the access opening in the skin, or through a cannula. Various types of entrapment devices are known in the art to facilitate this procedure.

Many entrapment devices are configured to decrease a volume of a tissue or otherwise reshape a tissue to facilitate a removal of the tissue. For example, a specimen retrieval bag including a morcellation means configured to percutaneously debulk tissue may be utilized. In another example, a specimen retrieval device includes a drawstring to decrease the volume of a specimen retrieval bag and a tissue therein. Entrapment devices are ideally of minimal volume and/or cross-section to facilitate a passage thereof through an opening and a maneuvering thereof in an internal cavity. There is a continuing need for improved specimen retrieval devices of decreased volume and improved maneuverability. There further remains a need for improved methods of removing a specimen from a bodily opening.

SUMMARY

In one aspect, a system for retrieving a tissue specimen is provided which includes a specimen retrieval bag having a first mating member and a retrieval device having a housing having a second mating member. The second mating member cooperates with the first mating member for coupling the bag with the retrieval device. A rotation mechanism is disposed in the retrieval device. Actuation of the rotation device draws an excess portion of the bag into the retrieval device.

The system may retract the excess portion of the bag into the housing of the retrieval device. The rotation mechanism may include a knob for actuating the rotation mechanism. The retrieval device may include a ratchet mechanism to inhibit rotation of the rotation mechanism in at least one direction. The first mating member may be a lip and the second mating member may be a slit. The retrieval device can include an inner member around which the bag is wound. In some embodiments, the first mating member is slid into engagement with the second mating member. In some embodiments, the rotation mechanism includes a slot having a first width and the housing includes a slot having a second width greater than the first width.

In another aspect, a method for retrieving a tissue specimen from a body cavity is provided which includes the steps of inserting a retrieval bag into the body cavity, placing a specimen into the bag, inserting a retrieval device into the body cavity, engaging the bag with the retrieval device, rotating an excess portion of the bag about an axis of the retrieval device to draw the excess portion of the bag into the retrieval device, and removing the retrieval device and the bag from the body cavity.

The step of engaging the bag may include engaging a lip of the bag with a slit of the retrieval device. The retrieval device in the method may include a knob and an axle for rotating the excess portion of the bag. The retrieval device may include a ratchet mechanism to inhibit rotation of the rotation mechanism in at least one direction. The rotating step may store the excess portion of the bag.

BRIEF DESCRIPTION OF THE DRAWINGS

Various embodiments of the present disclosure are described hereinbelow with references to the drawings, wherein.

DETAILED DESCRIPTION OF THE EMBODIMENTS

Embodiments of the present disclosure will now be described in detail with reference to the drawings, in which like reference numerals designate identical or corresponding elements in each of the several views. As used herein, the term "distal" refers to the portion of the instrument which is farthest from the user, while the term "proximal" refers to that portion of the instrument which is closest to the user. In the following description, well-known functions or constructions are not described in detail to avoid obscuring the present disclosure in unnecessary detail.

As used herein with reference to the present disclosure, the terms minimally invasive refer to instruments having a relatively narrow operating portion for insertion into a cannula, a small incision in the skin or through a body opening. Minimally invasive surgical procedures include for example laparoscopic, endoscopic, video assisted thoracic procedures, etc. It is believed that the present disclosure may find use in any procedure where access to the interior of the body is limited to a relatively small incision, with or without the use of a cannula, as in minimally invasive procedures.

Figure 1:
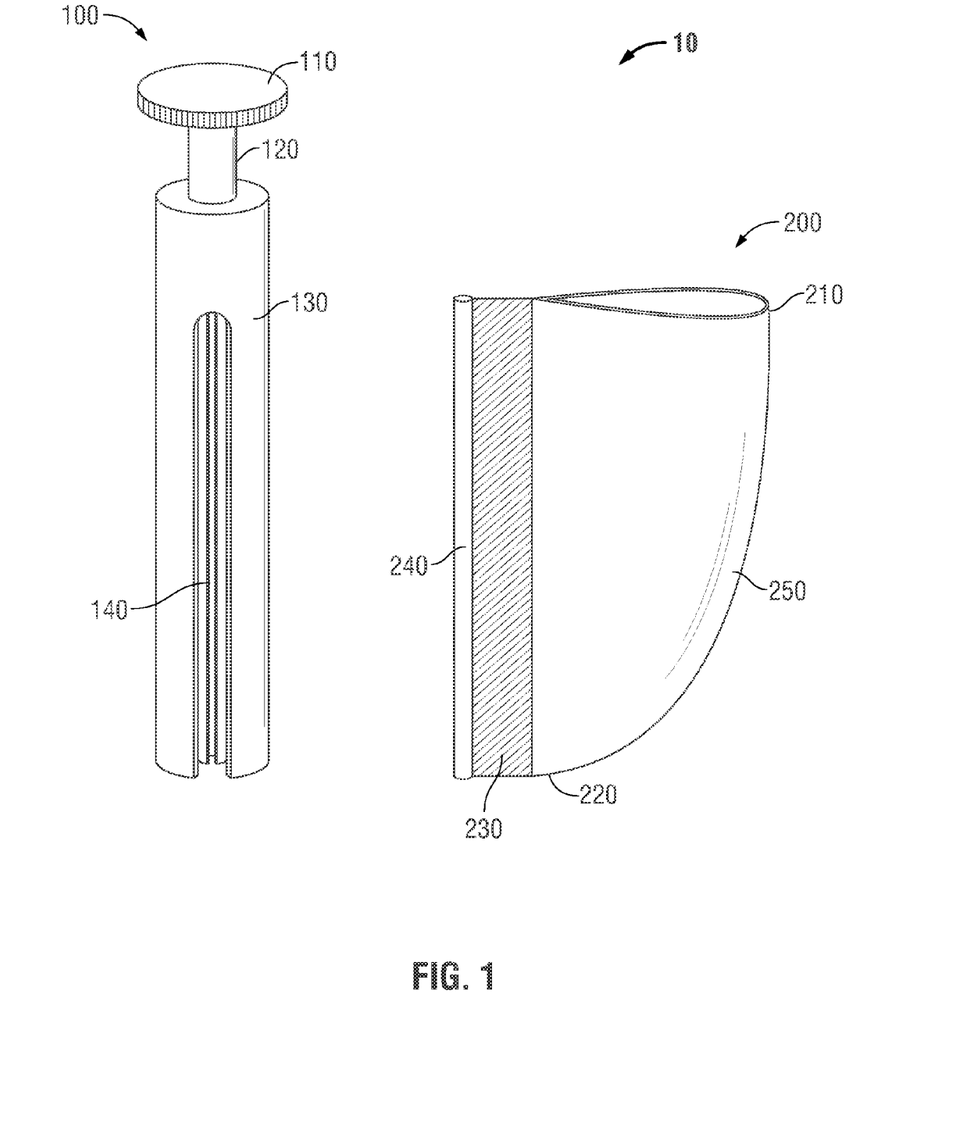
FIG. 1 is a side, perspective view of a specimen retrieval system according to the principles of the present disclosure.

With reference to FIG. 1, a specimen retrieval system 10 according to an embodiment of the present disclosure is illustrated. Specimen retrieval system 10 includes a retrieval device 100 and a collapsible specimen retrieval bag 200 configured for mating together. Specimen retrieval system 10 may be composed of any suitable biocompatible materials, such as biocompatible plastics.

Retrieval device 100 includes a knob 110, an axle 120, a housing 130, and a housing slit 140. Bag 200 includes a lip 240, a connection 230, and a body 250. Connection 230 interconnects lip 240 and body 250. Connection 230 is substantially flat. In one embodiment, lip 240 is substantially cylindrical. However, lip 240 may alternatively have any shape capable of mating with retrieval device 100.

Body 250 is sufficiently flexible to be rolled, folded, or otherwise compressed by retrieval device 100. Body 250 has an open end 210 and a closed end 220. Open end 210 is a proximal end of body 250, and closed end 220 is a distal end of body 250. Body 250 has a volume greater than a specimen "S" for receiving specimen "S" therein. Open end 210 allows a passage of material therethrough and has a perimeter sufficient for the passage of specimen "S" therethrough.

Figure 2:
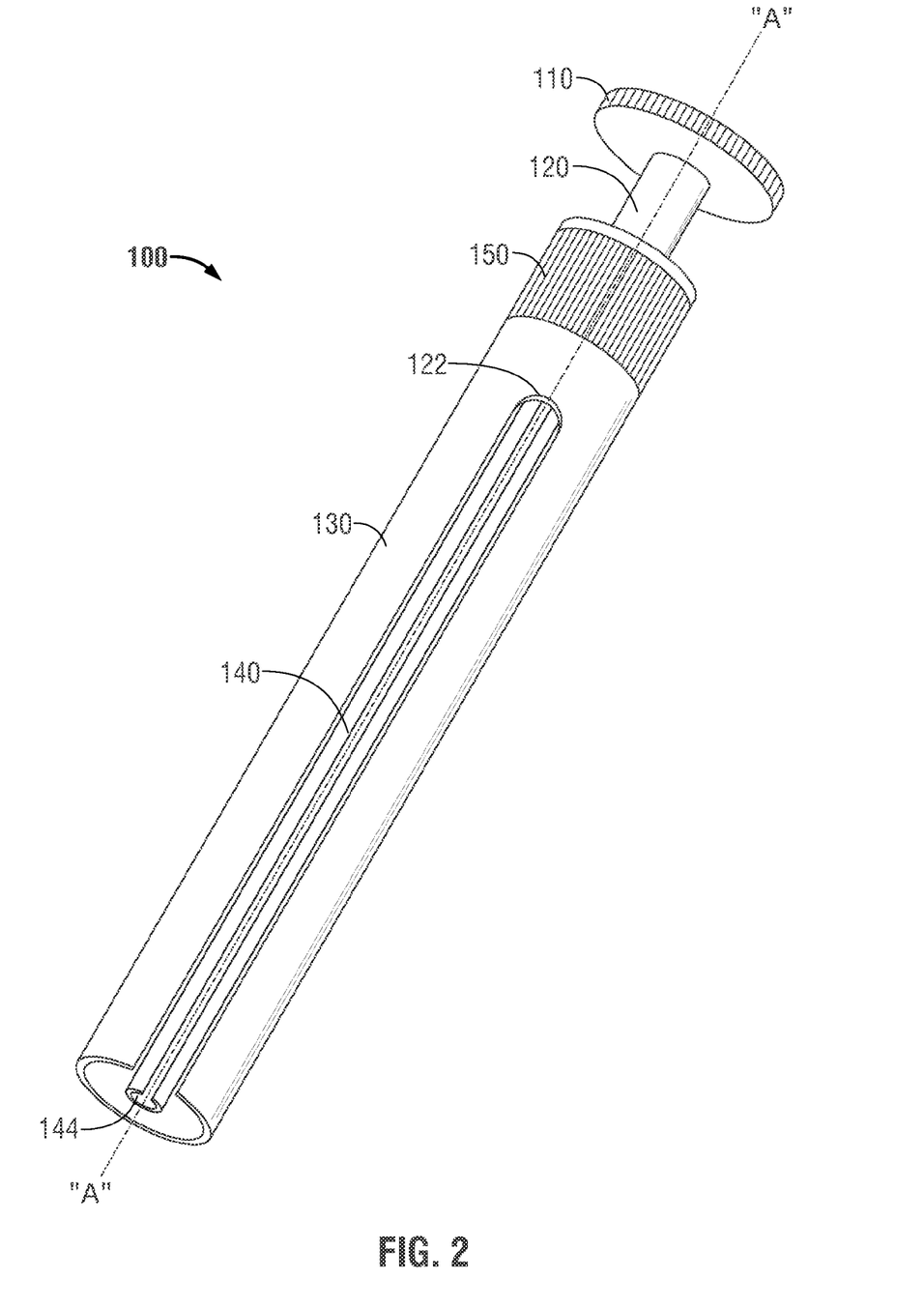
FIG. 2 is a side, perspective view of a retrieval device of the specimen retrieval system of FIG. 1.

Referring to FIG. 2, retrieval device 100 has a longitudinal axis "A" defined through axle 120. Knob 110 is located at a proximal end of retrieval mechanism 100 and is fixedly attached to axle 120, such that a rotation of knob 110 rotates axle 120. Axle 120 extends from knob 110 through housing 130. Housing 130 is a cylindrical, hollow structure configured for housing a ratchet mechanism 150, an inner member or axle segment 122 of axle 120, and a portion of bag 200. Housing 130 has a proximal end distal to knob 110. Ratchet mechanism 150 is located at the proximal end of housing 130 and provides for incremental rotation of axle 120. Axle segment 122 is located within housing 130 distal to ratchet mechanism 150. Axle segment 122 is hollow and configured for a receipt of lip 240. Housing slit 140 is an elongated opening in retrieval device 100 extending from a position distal to ratchet mechanism 150 to a distal end of housing 130.

Figure 3:
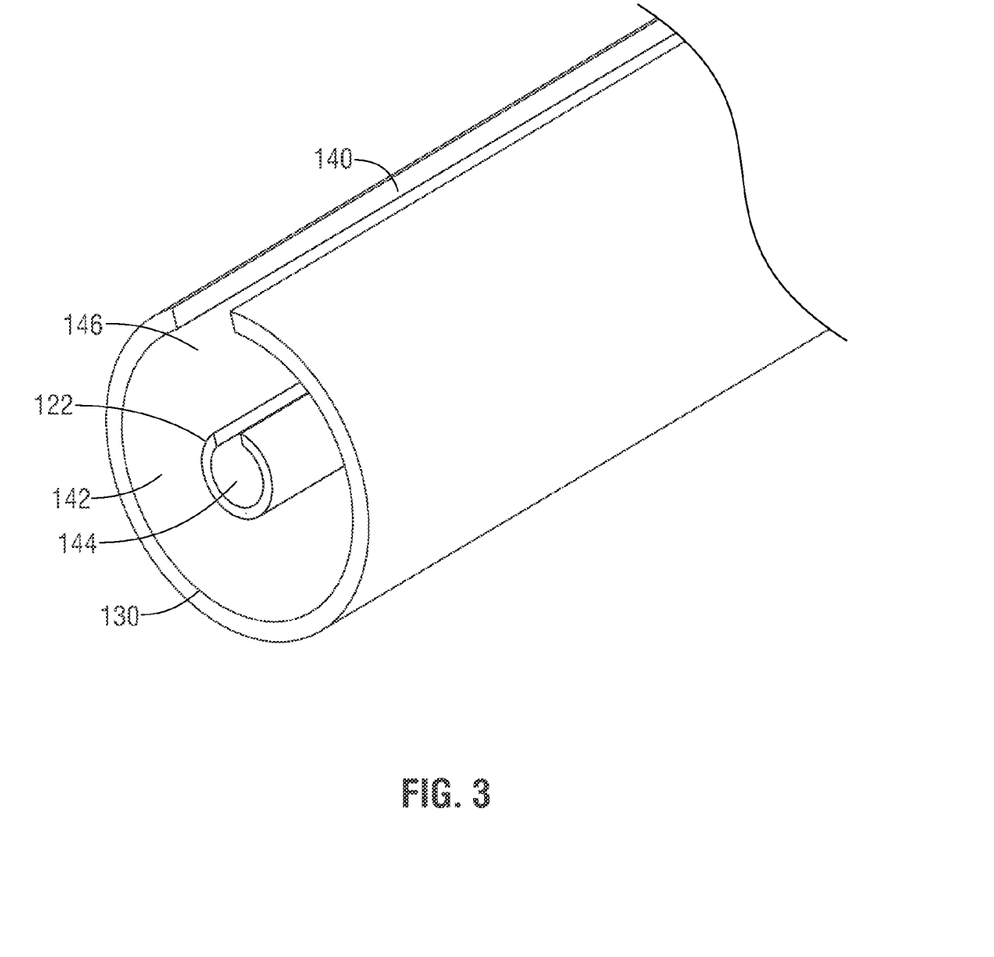
FIG. 3 is a bottom, perspective view of a distal end of the retrieval device of FIG. 2.

As seen in FIG. 3, axle segment 122 has a path 144 therein for receiving lip 240. Axle segment 122 has an axle slit 142 that may be aligned with housing slit 140 upon a rotation of axle 120. Axle slit 142 has a width less than a width of lip 240 to frictionally hold lip 240 within path 144. Housing slit 140 has a width "W₁" at least as wide as the width of lip 240 to allow lip 240 to enter path 144. A gap 146 exists between axle segment 122 and housing 130. Gap 146 is sufficiently large to allow a substantial portion of bag 200 to wrap around axle segment 122.

Figure 4A:
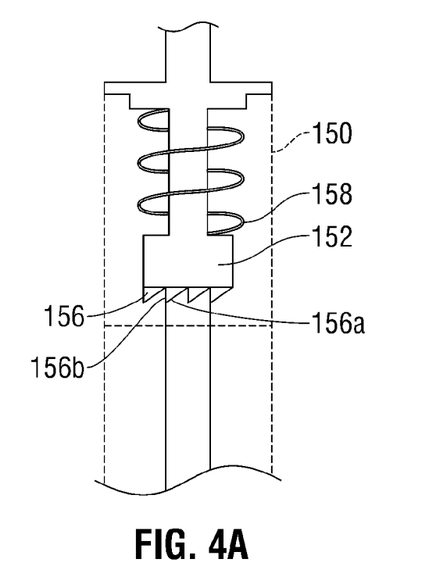
FIG. 4A is a side, perspective view of a ratchet mechanism of the retrieval device of FIG. 2.
Figure 4B:
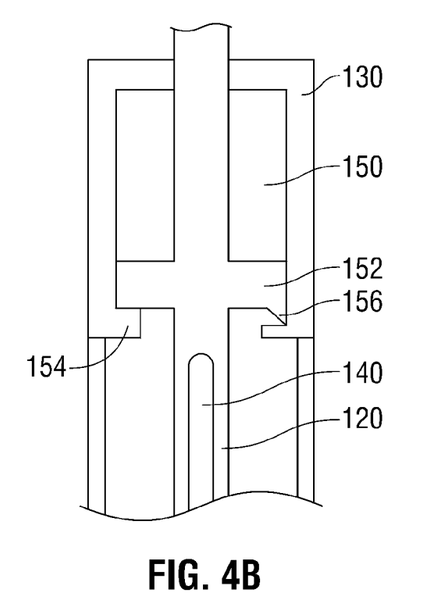
FIG. 4B is a side, cross-sectional view of the ratchet mechanism of FIG. 2.

Referring to FIGS. 4A-4B, ratchet mechanism 150 includes a gear 152, pawls 154, teeth 156, and a spring 158. At least one pawl 154 and at least one tooth 156 are provided, though various embodiments may have greater numbers of teeth and pawls. Gear 152 is concentric with axle 120, and gear 152 has a wider radius than a radius of axle 120. Teeth 156 extend distally from gear 152. Pawls 154 are fixedly attached to the inside of housing 130 in a position distal to gear 152 and in slidable contact with teeth 156. Spring 158 is positioned within housing 130 between a proximal end of gear 152 and a proximal end of housing 130. Spring 158 exerts a force that pushes gear 152 distally.

Each tooth 156 has an acute side 156a extending at an acute angle from gear 152 and a perpendicular side 156b extending perpendicularly from gear 152. Other configurations of teeth 156 that assist movement of gear 152 in a single direction are also contemplated, including arcuate teeth and teeth with sides extending from obtuse angles from gear 152. Alternatively, it may be desirable for teeth 156 to have two acute sides 156a if bidirectional movement of gear 152 is needed.

A rotation of knob 110 in a first direction rotates axle 120 in the first direction and further rotates gear 152 in the first direction. The rotation of gear 152 in the first direction places at least one side 156a into contact with at least one pawl 154. Contact of a side 156a with a pawl 154 during rotation of gear 152 in the first direction causes a tooth 156 to slide proximally along the pawl 154 and translate gear 152 proximally along axis "A". When the tooth 156 is fully proximal to the pawl 154, the rotation of gear 152 in the first direction rotates the tooth 156 in the first direction until the tooth 156 is no longer in contact with the pawl 154, allowing the force of spring 158 to push gear 152 distally until the tooth 156 is no longer fully proximal to the pawl 154. Side 156b is configured such that rotational contact thereof with a pawl 154 does not cause the side 156b to slide proximally along the pawl 154, thus inhibiting gear 152 from rotating in a second direction.

Figure 5A:
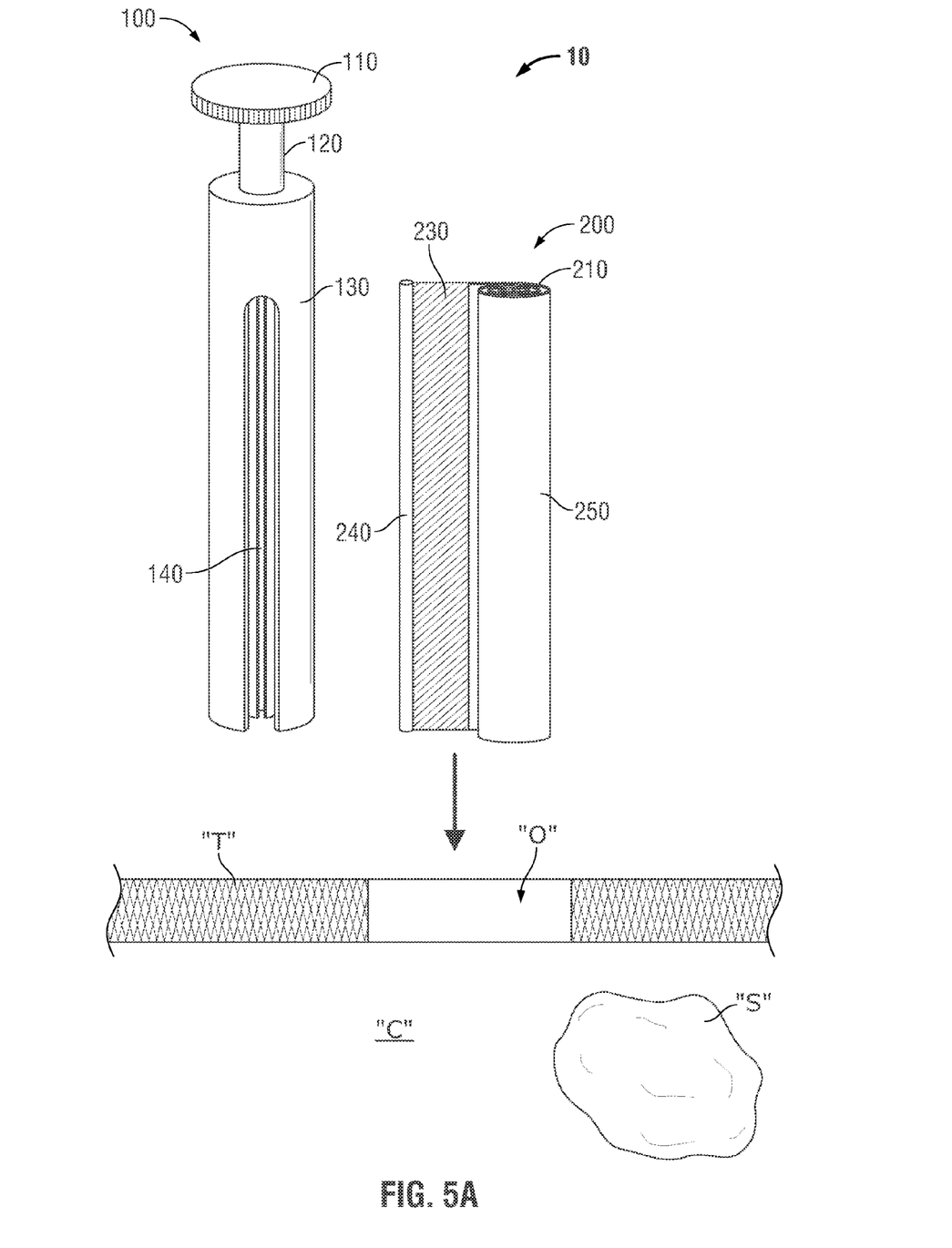
FIGS. 5A-5D are side perspective views of the specimen retrieval system of FIG. 1 removing a tissue from a body cavity through an opening.
Figure 5B:
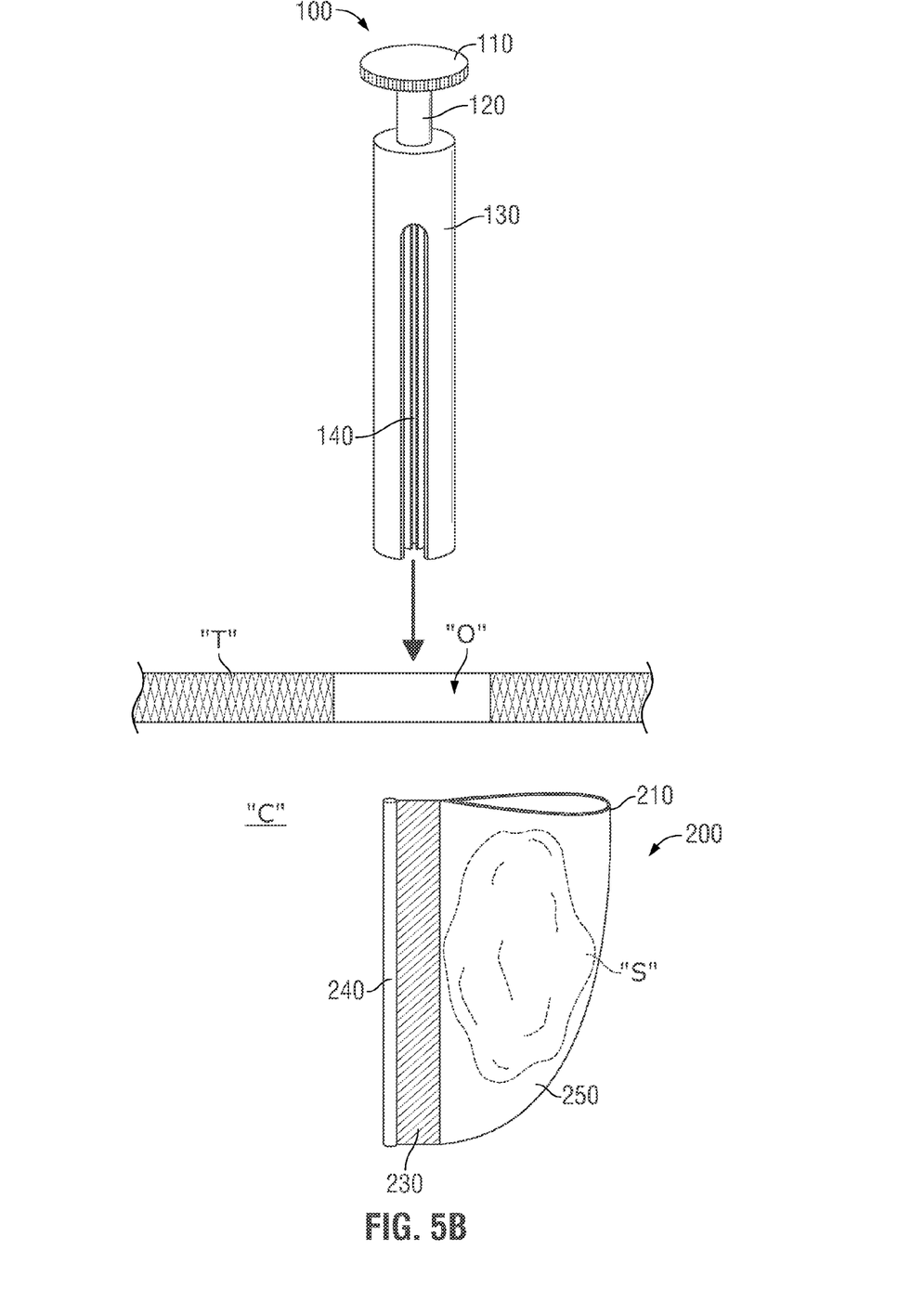

Turning to FIGS. 5A-5D, an exemplary method of use of specimen retrieval system 10 is illustrated. Any commonly known surgical tool, such as surgical forceps, may be suitable for manipulating specimen retrieval system 10 according to this method. As seen in FIG. 5A, a tissue specimen "S" lies in a cavity "C" underlying a tissue "T". An opening "O" exists in tissue "T" and is sufficiently wide for allowing a passage of specimen retrieval system 10 therethrough. An access port (not shown) can be inserted through the opening "O" through which system 10 is inserted. First, a cross-sectional area of bag 200 is decreased for insertion through opening "O" for example, through a rolling or folding of body 250. As seen in FIG. 5B, bag 200 may be expanded within cavity "C" by a surgical instrument such as a grasper (not shown) to allow an insertion of specimen "S" therein. Specimen "S" is inserted through open end 210 and placed in bag 250. The bag 250 is thus inserted into the body cavity "C" without the housing 130, and can remain in body cavity "C" without the housing 130 during the surgical procedure, until removal is desired. The absence of such elongated housing during the surgery facilitates access and maneuverability within the cavity "C".

Figure 5C:
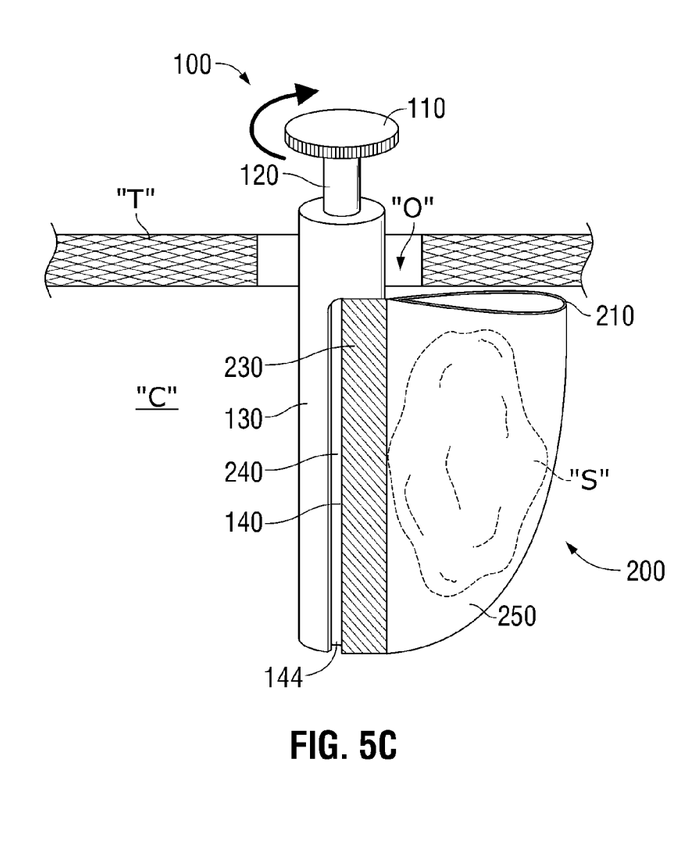
Figure 5D:
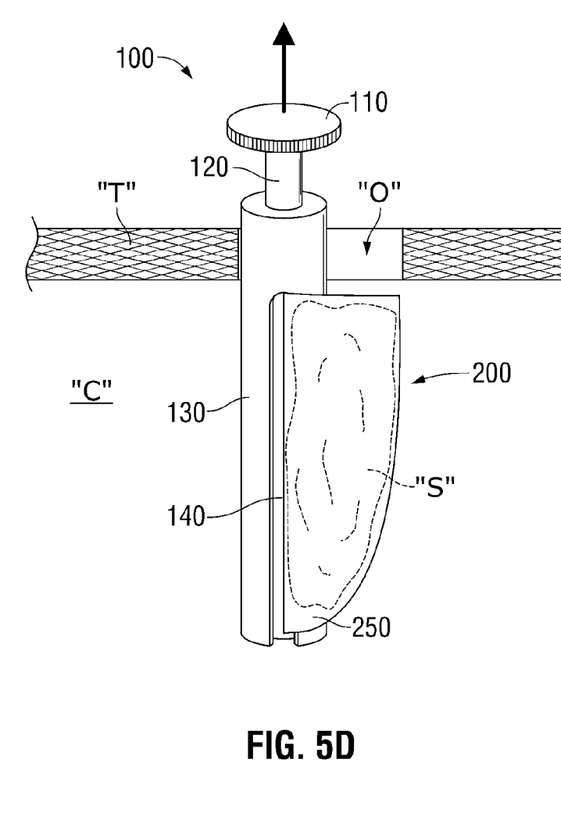

As seen in FIG. 5C, when it is desired to remove the bag, retrieval device 100 is inserted through opening "O" and mated with bag 200. Lip 240 is inserted through path 144 and connection 230 is inserted through housing slit 140 and axle slit 142. Knob 110 may then be rotated to retract an excess portion of bag 200 into gap 160 within housing 130, which decreases a volume and/or cross-section of bag 250 and may compress specimen "S". Such reduction in bag size and specimen compression facilitates removal. Ratchet mechanism 150 inhibits the excess portion of bag 250 from returning outside housing 130. As seen in FIG. 5D, retrieval device 100 compresses bag 250 until specimen retrieval device 10 has a sufficiently small cross section to pass through opening "O". At this point, specimen retrieval device 10 may be lifted proximally through opening "O" to complete a removal thereof.

As can be appreciated, being able to adjust the size of the bag while still in the body cavity, after the specimen is inserted, allows the use of a larger size bag. It also allows a single sized bag to be used for a wide range of specimen sizes as the bag size can be adjusted in situ, rather than relying on different size bags for different size specimens.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method for retrieving a tissue specimen from a body cavity, comprising: inserting a specimen retrieval bag into the body cavity; placing a specimen into the retrieval bag; inserting a retrieval device into the body cavity; engaging the retrieval bag with the retrieval device; wherein engaging the retrieval bag includes disposing a lip of the retrieval bag in a slot of the retrieval device; rotating an excess portion of the retrieval bag about an axis of the retrieval device to draw the excess portion of the retrieval bag into the retrieval device; wherein the retrieval device includes a ratchet mechanism to inhibit rotation of the inner member in at least one direction; and removing the retrieval device and the retrieval bag from the body cavity.

2. The method according to claim 1, wherein the retrieval device includes:
   a knob; and
   an inner member extending from the knob such that rotation of the knob effects rotation of the inner member to rotate the excess portion of the retrieval bag.

3. The method according to claim 1, wherein rotating the excess portion stores the excess portion in a gap defined between a housing of the retrieval device and an inner member of the retrieval device that is received within the housing.

4. A method for retrieving a tissue specimen from a body cavity, comprising: positioning a tissue specimen in a collapsible bag, the collapsible bag being coupled to a rotation mechanism of a retrieval device; wherein engaging the retrieval bag includes disposing a lip of the retrieval bag in a slot of the retrieval device; rotating the rotation mechanism of the retrieval device relative to a housing of the retrieval device to draw a portion of the collapsible bag into a gap defined between the housing and the rotation mechanism; wherein the retrieval device includes a ratchet mechanism to inhibit rotation of the inner member in at least one direction; and removing the collapsible bag and the retrieval device from the body cavity.

5. The method according to claim 4, wherein positioning the tissue specimen in the collapsible bag includes passing the tissue specimen through an open, proximal end of the collapsible bag.

6. The method according to claim 4, wherein the portion of the collapsible bag is drawn into the gap in a direction that is perpendicular to a longitudinal axis defined by the retrieval device.

7. The system according to claim 4, wherein at least a portion of a proximal end and a distal end of the collapsible bag are drawn into the gap.

8. The method according to claim 4, wherein rotating the rotation mechanism includes rotating a knob of the rotation mechanism to wind the portion of the collapsible bag about an inner member of the rotation mechanism.

* * * * *